(12) United States Patent
Hazebrouck et al.

(10) Patent No.: US 7,481,841 B2
(45) Date of Patent: Jan. 27, 2009

(54) ADJUSTABLE ORTHOPAEDIC PROSTHESIS AND ASSOCIATED METHOD

(75) Inventors: Stephen A. Hazebrouck, Winona Lake, IN (US); Mark B. Lester, Warsaw, IN (US); Charles A. Andrade, Jr., Westbrook, CT (US); Joshua R. Murphy, Unoasville, CT (US); Sheryl L.A. Andrade, Westbrook, CT (US)

(73) Assignee: DePuy Products, Inc., Warsaw, IN (US)

( * ) Notice: Subject to any disclaimer, the term of this patent is extended or adjusted under 35 U.S.C. 154(b) by 613 days.

(21) Appl. No.: 10/880,859

(22) Filed: Jun. 30, 2004

(65) Prior Publication Data
US 2006/0004459 A1    Jan. 5, 2006

(51) Int. Cl.
*A61F 2/30* (2006.01)
(52) U.S. Cl. .................................... 623/18.12
(58) Field of Classification Search .............. 623/16.11, 623/18.11, 18.12, 20.14, 20.24, 20.25
See application file for complete search history.

(56) References Cited

U.S. PATENT DOCUMENTS

| | | | |
|---|---|---|---|
| 3,976,060 A | 8/1976 | Hildebrandt et al. |
| 3,986,504 A | 10/1976 | Avila |
| 4,024,588 A | 5/1977 | Janssen et al. |
| 4,091,806 A | 5/1978 | Aginsky |
| 4,157,715 A | 6/1979 | Westerhoff |
| 4,190,044 A | 2/1980 | Wood |
| 4,262,665 A | 4/1981 | Roalstad et al. |
| 4,275,717 A | 6/1981 | Bolesky |
| 4,384,373 A | 5/1983 | Sivash |
| 4,453,539 A | 6/1984 | Raftopoulos et al. |
| 4,502,160 A | 3/1985 | Moore et al. |
| 4,520,511 A | 6/1985 | Gianezio et al. |
| 4,681,590 A | 7/1987 | Tansey |
| 4,892,546 A | 1/1990 | Kotz et al. |
| 4,946,459 A | 8/1990 | Bradshaw et al. |
| 5,057,103 A | 10/1991 | Davis |
| 5,059,193 A | 10/1991 | Kuslich |
| 5,071,435 A | 12/1991 | Fuchs et al. |
| 5,074,882 A | 12/1991 | Grammont et al. |
| 5,102,413 A | 4/1992 | Poddar |
| 5,108,398 A | 4/1992 | McQueen et al. |
| 5,123,926 A | 6/1992 | Pisharodi |
| 5,236,460 A | 8/1993 | Barber |
| 5,263,955 A | 11/1993 | Baumgart et al. |
| 5,326,360 A | 7/1994 | Kotz et al. |

(Continued)

FOREIGN PATENT DOCUMENTS
WO    WO 1990-02533    3/1990

(Continued)

OTHER PUBLICATIONS

Webpage obtained through http://www.wmt.com/Patients/oncology/repiphysis.asp. "Oncology Repiphysis", 1 page, printed on May 25, 2004.

(Continued)

*Primary Examiner*—Anu Ramana
(74) *Attorney, Agent, or Firm*—Barnes & Thornburg LLP (57) ABSTRACT

An adjustable prosthesis includes an actuator for adjusting the prosthesis subsequent to surgical implantation thereof. The actuator is activated by application of an trans-cutaneous signal. A method of operating an adjustable prosthesis is also disclosed.

33 Claims, 6 Drawing Sheets

U.S. PATENT DOCUMENTS

| | | | |
|---|---|---|---|
| 5,350,379 | A | 9/1994 | Spievack |
| 5,356,411 | A | 10/1994 | Spievack |
| 5,358,524 | A | 10/1994 | Richelsoph |
| 5,364,396 | A | 11/1994 | Robinson et al. |
| 5,415,660 | A | 5/1995 | Campbell et al. |
| 5,429,638 | A | 7/1995 | Muschler et al. |
| 5,466,261 | A | 11/1995 | Richelsoph |
| 5,505,733 | A | 4/1996 | Justin et al. |
| 5,516,335 | A | 5/1996 | Kummer et al. |
| 5,536,269 | A | 7/1996 | Spievack |
| 5,575,790 | A | 11/1996 | Chen et al. |
| 5,626,579 | A | 5/1997 | Muschler et al. |
| 5,626,581 | A | 5/1997 | Staehlin et al. |
| 5,665,122 | A | 9/1997 | Kambin |
| 5,700,263 | A | 12/1997 | Schendel |
| 5,704,938 | A | 1/1998 | Staehlin et al. |
| 5,704,939 | A | 1/1998 | Justin |
| 5,720,746 | A | 2/1998 | Soubeiran |
| 5,827,286 | A | 10/1998 | Incavo et al. |
| 5,846,245 | A | 12/1998 | McCarthy et al. |
| 5,855,580 | A | 1/1999 | Kriedler et al. |
| 5,879,386 | A | 3/1999 | Jore |
| 5,885,283 | A | 3/1999 | Gittleman |
| 5,885,290 | A | 3/1999 | Guerrero et al. |
| 5,895,387 | A | 4/1999 | Guerrero et al. |
| 5,902,304 | A | 5/1999 | Walker et al. |
| 5,961,553 | A | 10/1999 | Coty et al. |
| 6,025,537 | A | 2/2000 | Werding et al. |
| 6,033,412 | A | 3/2000 | Losken et al. |
| 6,036,690 | A | 3/2000 | De La Plaza Fernandez |
| 6,077,265 | A | 6/2000 | Werding et al. |
| 6,106,525 | A | 8/2000 | Sachse |
| 6,113,599 | A | 9/2000 | Landsberger |
| 6,127,597 | A | 10/2000 | Beyar et al. |
| 6,187,004 | B1 | 2/2001 | Fearon |
| 6,200,317 | B1 | 3/2001 | Aalsma et al. |
| 6,224,600 | B1 | 5/2001 | Protogirou |
| 6,245,075 | B1 | 6/2001 | Betz et al. |
| 6,261,289 | B1 | 7/2001 | Levy |
| 6,277,124 | B1 | 8/2001 | Haag |
| 6,336,929 | B1 | 1/2002 | Justin |
| 6,358,283 | B1 | 3/2002 | Högfors et al. |
| 6,383,185 | B1 | 5/2002 | Baumgart |
| 6,416,516 | B1 | 7/2002 | Stauch et al. |
| 6,425,923 | B1 | 7/2002 | Stalcup et al. |
| 6,447,514 | B1 | 9/2002 | Stalcup et al. |
| 6,447,515 | B1 | 9/2002 | Meldrum |
| 6,520,991 | B2 | 2/2003 | Huene |
| 6,554,833 | B2 | 4/2003 | Levy et al. |
| 6,565,576 | B1 | 5/2003 | Stauch et al. |
| 6,613,052 | B1 | 9/2003 | Kinnett |
| 6,673,079 | B1 | 1/2004 | Kane |
| 6,706,042 | B2 | 3/2004 | Taylor |
| 6,730,087 | B1 | 5/2004 | Butsch |
| 6,736,818 | B2 | 5/2004 | Perren et al. |
| 6,755,862 | B2 | 6/2004 | Keynan |
| 6,783,530 | B1 | 8/2004 | Levy |
| 6,796,984 | B2 | 9/2004 | Soubeiran |
| 7,135,022 | B2 * | 11/2006 | Kosashvili et al. ............ 606/63 |
| 2003/0204267 | A1 | 10/2003 | Hazebrouck et al. |
| 2004/0030395 | A1 | 2/2004 | Blunn et al. |
| 2004/0133204 | A1 | 7/2004 | Davies |
| 2004/0138663 | A1 | 7/2004 | Kosashvili et al. |
| 2004/0167625 | A1 | 8/2004 | Beyar et al. |
| 2004/0193266 | A1 | 9/2004 | Meyer |
| 2004/0193267 | A1 | 9/2004 | Jones et al. |
| 2004/0193268 | A1 | 9/2004 | Hazebrouck |

FOREIGN PATENT DOCUMENTS

| | | | |
|---|---|---|---|
| WO | WO 00/44315 | | 8/2000 |
| WO | WO 00/44319 | | 8/2000 |
| WO | WO00/48524 | | 8/2000 |
| WO | WO 01/54598 | | 8/2001 |
| WO | WO0178614 | A1 * | 10/2001 |

OTHER PUBLICATIONS

Webpage obtained through http://www.ortholumormd.com/pages/specialchildren.php, "Musculo-skeletal tumor orthopaedic practice, published works: special considerations for growing children", 10 pages, printed on May 25, 2004.

Walker, J. "On the cutting edge of prosthetics, Precision Machine launches new design for artificial hip", *Pictorial Gazette*, 2 pages, Jun. 24, 2003.

Szabo, Liz, USA Today, "Experimental implant grows with young limbs; technology spares bone cancer patients painful surgeries," Jul. 13, 2004, p. D.8.

Webpage obtained through http://www.news.bbc.co.uk/2/hi/health/3917573.stm, Jackson, Melissa, "Bionic therapy for leg bones," 3 pages, printed Aug. 6, 2004.

Sharke, Paul, "The machinery of life," *Mechanical Engineering*, Feb., 2004, pp. 30-34.

Webpage obtained through http://www.designnews.com/index.asp?layout=articlePrint&articleID=CA426260, "Drive implant eliminates follow-up surgery," 2 pages, printed Jul. 28, 2004.

Dominkus, M. (2001) "Growth Predictions in Extendable Tumor Prostheses in Children," Clinical Orthopaedics and Related Research, Sep. 2001, No. 390, pp. 212-220.

Ries Lag, Smith Ma, Gurney Jg, Linet M, Tamra T, Young Jl, Bunin Gr (eds), Cancer incidence and survival among children and adolescents: U.S. SEER Program 1975-1995, National Cancer Institute, NIH Pub. No. 99-4649, Bethesda, MD, 1999, Gurney et al Chapter entitled "Malignant Bone Tumors," pp. 100-110.

Eckardt, Jj et al. "Expandable endoprosthesis reconstruction in skeletally immature patients with tumors." Clin. Orthop. 2000 Apr. (373) pp. 51-61.

Verkeke Gj, et al. "Design of a lengthening element for a modular femur endoprosthetic system," Proc. Inst. Mech. Eng. [H], 1989; 203(2) pp. 97-102.

Verkerke Gj et al. "First clinical experience with a noninvasively extendable endoprosthesis: a limb-saving procedure in children suffering from a malignant bone tumor." Artif Organs. 1997 May; 21(5) pp. 413-417.

Memphis Business Journal "Wright Medical gets FDA clearance for repiphysis technology," Dec. 5, 2002.

Wilkins R., Souberain A. "The Phenix Expandable Prosthesis: Early American Experience." Clin. Orthop 2001 Jan; (382) pp. 51-58.

Cole, Jd et al. "The intramedullary skeletal kinetic distractor (ISKD); first clinical results of a new intramedullary nail for lengthening of the femur and tibia", *Injury*, Dec., 2001, 32 Suppl 4, pp. 129-139.

Neel, M and Letson, G. "Modular endoprostheses for children with malignant bone tumors," Cancer Control, Jul./Aug. 2001, v. 8, n.4, pp. 344-348.

Tudor-Locke, C, et al; "The relationship between pedometer-determined ambulatory activity and body composition variables." Int. J. Obes. Nov. 2001; 25 (11), pp. 1571-1578.

Schmalzried, Tp, et al; "Quantitative assessment of walking activity after total hip or knee replacement." J Bone Joint Surg Am. Jen., 1998 80 (1); pp. 54-59.

Gaebler, C, et al.; "A new modular testing system for biomechanical evaluation of tibial intramedullary fixation devices. Injury;" Nov. 2001, 32(9); pp. 708-712.

Guichett, Jm, et al; "Mechanical characterization of a totally intramedullary gradual elongation nail." Clin. Orthop. Apr., 1997; (337): pp. 281-290; obtained from www.corronline.com on Jan. 6, 2005; 13 pages.

European Search Report dated Nov. 25, 2005 (5 pages).

Office action dated Aug. 13, 2007 issued in co-pending 11/154,339 patent application.

* cited by examiner

ADJUSTABLE ORTHOPAEDIC PROSTHESIS AND ASSOCIATED METHOD

FIELD OF THE DISCLOSURE

The present disclosure relates generally to orthopaedic prostheses and methods of using the same.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a hip replacement procedure, a femoral prosthesis is implanted into the patient's femur. The femoral prosthesis typically includes an elongated stem component which is implanted into the medullary canal of the patient's femur and a spherically-shaped head which bears against the patient's acetabulum or a prosthetic replacement acetabular cup. In the case of a shoulder replacement procedure, a humeral prosthesis is implanted into the patient's humerus. The humeral prosthesis includes an elongated stem component which is implanted into the medullary canal of the patient's humerus and a spherically-shaped head which bears against the patient's glenoid or a prosthetic replacement glenoid component. In the case of a knee replacement procedure, a tibial prosthesis is implanted into the patient's tibia. The condyle surfaces of the patient's femur, or the condyle surfaces of a replacement femoral component, bear against the tibial prosthesis.

Subsequent to implantation, there is occasionally the need to adjust the prosthesis. For example, it may be necessary to adjust the prosthesis to correct a surgical error or correct for subsidence of the implant. Such adjustments necessitate one or more revision surgeries.

Moreover, each year in the United States approximately 650-700 children under the age twenty (20) are diagnosed with a malignant bone tumor. When presented with these types of cases, the surgeon can either amputate the entire limb or try to preserve it. To preserve the limb, the cancerous portion of the bone is removed. This surgery typically involves the removal of one or both of the growth plates. Because the residual bone cannot grow at the same speed as the contra lateral bone, a modular endoprosthesis is often implanted. As the child grows, more surgeries are required to lengthen the device. Depending on the age and condition of the patient, the number of surgeries that the patient has to endure can be greater than twenty. Specifically, for the young patient to grow properly with an modular endoprosthesis, multiple surgeries must be completed to continually lengthen the device or replace it with a new, longer one. After the patient has reached his/her full height, it may be necessary to replace the endoprosthesis again with a permanent endoprosthesis.

SUMMARY

According to one aspect of the present disclosure, an adjustable prosthesis includes a first component which may be moved relative to a second component by use of an trans-cutaneous signal.

The prosthesis may include a telescoping stem having an adjustable length.

The prosthesis may include a long bone prosthesis having an adjustable length and an adjustable offset.

The prosthesis may be bi-directionally adjustable along one or more axes of movement.

The prosthesis may include a tibial component.

The trans-cutaneous signal may include a magnetic field.

According to another aspect of the present disclosure, there is provided a method of operating an implantable prosthesis. The method includes implanting the prosthesis and thereafter post-operatively adjusting the prosthesis.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Referring now to FIGS. 1-7, there is shown an adjustable femoral prosthesis 20 for implantation into a patient's femur during performance of a hip replacement procedure. It should be appreciated that although the concepts of the present disclosure are herein exemplarily described in regard to a prosthesis for use in the performance of a hip replacement procedure, the concepts of the present disclosure may be utilized in regard to a prosthesis for implantation into other bones of the body. For example, the concepts of the present disclosure may be utilized in the construction of a prosthesis for implantation into the humerus, radius, ulna, tibia, fibula, or any of the metatarsals or metacarpals.

Figure 1:
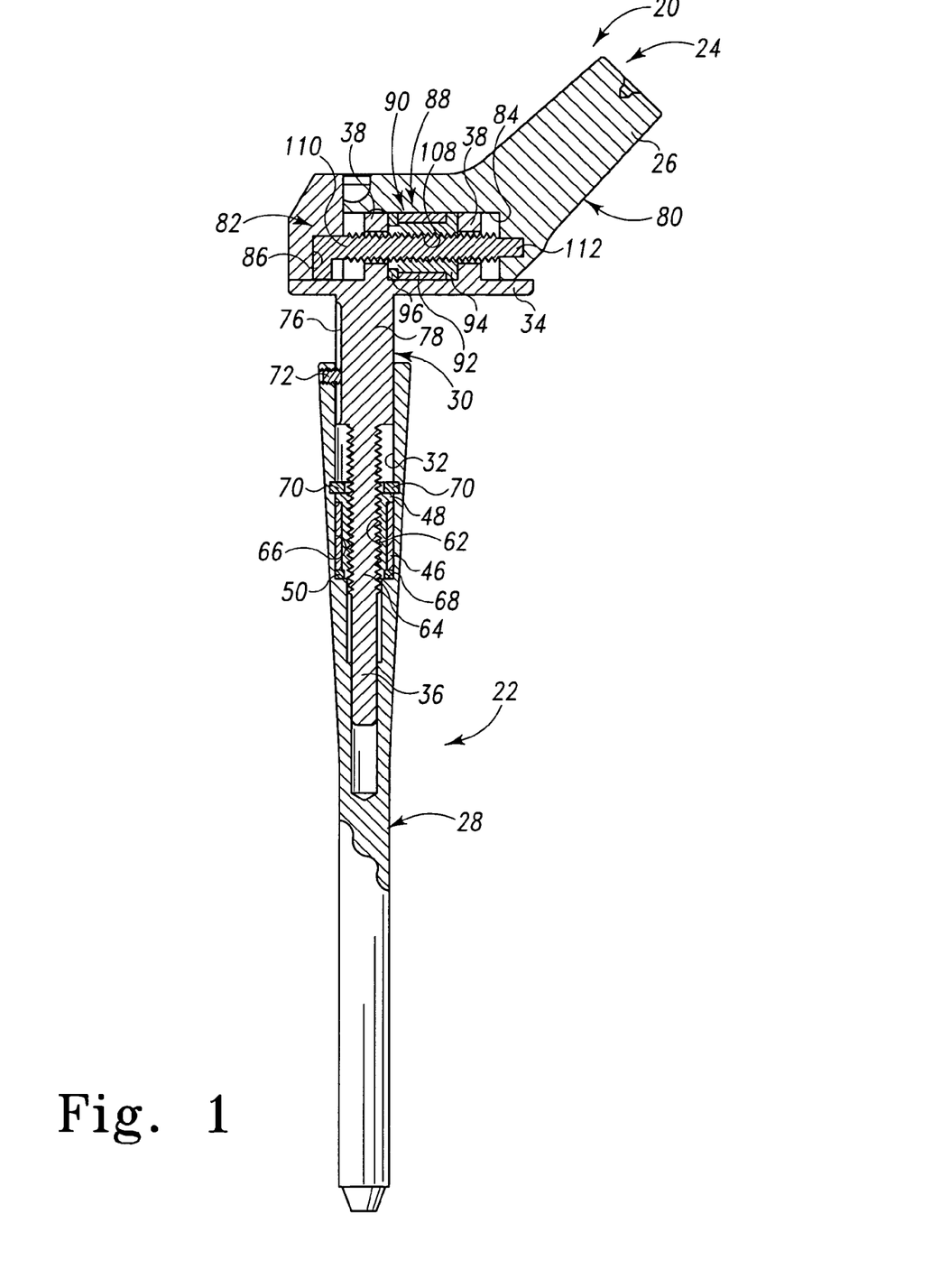
FIG. 1 is a cross sectional view of an adjustable femoral prosthesis.

The femoral prosthesis 20 includes a stem 22 and a head 24. The prosthesis 20 is configured to be implanted into the femur of a patient in order to replace certain natural features of the patient's femur as a result of, for example, disease or trauma. The prosthesis 20 is implanted into a surgically prepared (e.g., reamed and/or broached) medullary canal of the femur.

The stem 22 and the head 24 of the prosthesis 20 may be utilized to secure the patient's femur for movement relative to the patient's pelvis. In particular, a portion of the head 24 is positioned to bear on either the patient's natural acetabulum or a prosthetic socket in the form of a prosthetic cup (not shown) which has been implanted into the patient's pelvis to replace his or her acetabulum. In such a manner, the prosthesis 20 and the natural or artificial acetabulum collectively function as a system which replaces the natural "ball and socket" joint of the patient's hip.

Both the stem 22 and the head 24 may be made of materials conventionally utilized in the construction of prosthetic implants. For example, the stem 22 and the head 24 may be constructed from implantable metals such as stainless steel, cobalt chrome, or titanium. The stem 22 and the head 24 may also be constructed with non-metallic materials such as implant-grade polymers or ceramics.

The stem 22 may be embodied in a number of different configurations in order to fit the needs of a given patient's anatomy and provide a variety of geometries and sizes. In particular, the stem 22 may be configured in various different lengths to conform to the patient's anatomy (e.g., a relatively long stem 22 for use with a long femur, a relatively short stem 22 for use with a short femur, etcetera). Moreover, the stem 22 may also be embodied in a bow-shaped configuration if required by a given patient's anatomy. Yet further, the stem 22 may also be embodied in various diameters as required by a given patient's anatomy.

The head 24 includes a neck 26 extending outwardly from the body thereof. A generally spherically shaped prosthesis (not shown) that mimics a natural femoral head is taper fit or otherwise secured to the neck 26.

The stem 22 is implanted into an elongated bore surgically formed in the patient's femur. As such, the stem 22 may be constructed with materials which promote bone ingrowth into the outer surfaces of the stem 22. Moreover, since bone cement may be used to secure the stem 22 in the femur, the materials from which the stem 22 is constructed may also be selected to promote interdigitation of bone cement into the outer surfaces of the stem 22.

Figure 4:
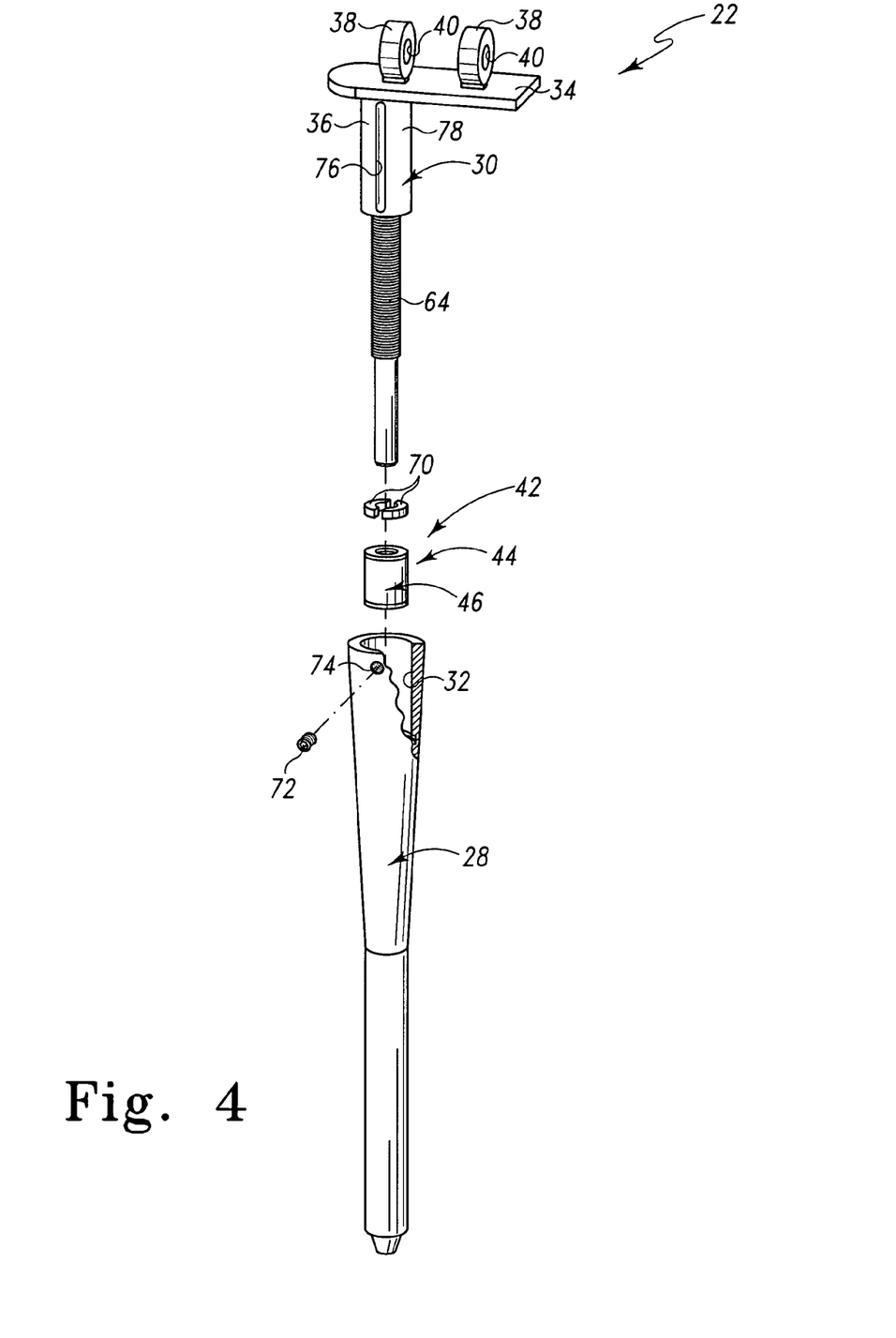
FIG. 4 is an exploded perspective view of the stem of the femoral prosthesis of FIG. 1.

As shown in FIGS. 1 and 4, the stem 22 includes a pair of telescoping stem components. In the exemplary embodiment described herein, the stem 22 includes an outer shell 28 with a stem shaft 30 telescoping outwardly therefrom. The outer shell 28 has an elongated bore 32 defined therein. As shown in FIG. 1, a distal end of the stem shaft 30 is positioned in the elongated bore 32, whereas the proximal end of the stem shaft 30 extends out of the bore 32. The bore 32 is stepped in configuration having a number of bore sections with differing diameters, each of which shares a common center line.

The stem shaft 30 includes a platform 34 having a shaft 36 extending downwardly from a bottom surface thereof. The shaft 36 is stepped in configuration having a number of shaft sections with differing diameters, each of which shares a common center line. The platform 34 has a pair of flanges 38 secured to an upper surface thereof. Each of the flanges 38 has a hole 40 defined therein. As will be described in greater detail below, an actuator for adjusting the offset of the femoral prosthesis 20 is positioned between the flanges 38.

The stem shaft 30 is moved relative to the outer shell 28 by an actuator 42. The actuator 42 may be embodied as any type of actuator for post-operatively telescoping or otherwise moving the stem shaft 30 relative to the outer shell 28. As will herein be described in more detail, the actuator 42 is operable to bi-directionally move the stem shaft 30 relative to the outer shell 28. In particular, the actuator 42 is operable to extend the stem shaft 30 out of the outer shell 28 thereby increasing the length of the prosthesis 20, and is also operable to retract the stem shaft 30 into the outer shell 28 thereby decreasing the length of the prosthesis 20. In the exemplary embodiment described herein, the actuator 42 is embodied as a magnetic drive actuator 44 that is operated by an external (e.g., transcutaneous) electromagnetic source.

Figures 2, 3:
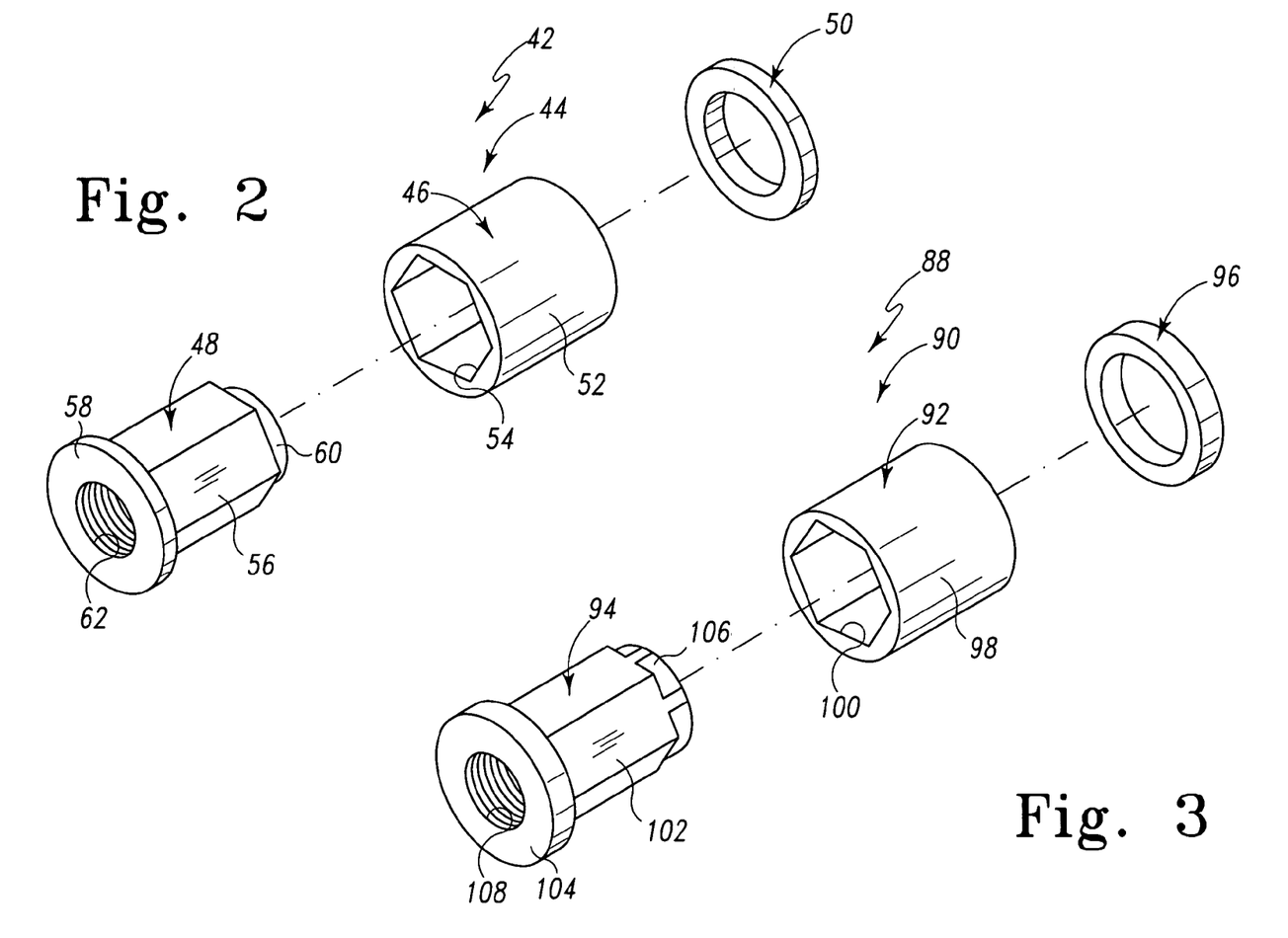
FIG. 2 is an exploded perspective view of a magnetic drive actuator that is operable to adjust the length of the femoral prosthesis of FIG. 1.
FIG. 3 is an exploded perspective view of a magnetic drive actuator that is operable to adjust the offset of the femoral prosthesis of FIG. 1.

As shown in FIG. 2, the magnetic drive actuator 44 includes a magnet 46, a sleeve 48, and a cap 50. The magnet 46 may be constructed with any type of implantable magnetic material, whereas the sleeve 48 and the cap 50 may be made from implantable non-magnetic materials such as cobalt chrome or titanium. In the exemplary embodiment described herein, the magnet 46 is embodied as a cylindrically-shaped body 52 having a bore 54 extending therethrough. The bore 54 has an internal hex-shaped configuration which corresponds with an external hex-shaped body 56 of the sleeve 48. An annular flange 58 is secured to one end of the hex-shaped body 56 of the sleeve 48. A annular rim 60 is secured to the other end of the hex-shaped body 56 of the sleeve 48. As shown in FIG. 2, the cap 50 is press fit or otherwise secured onto the rim 60. As such, the magnet 46 is retained on the sleeve 48 on one end by the flange 58 and on the other end by the cap 50. The interface of the hex-shaped surfaces facilitates transfer of rotational force from the magnet 46 to the sleeve 48. The sleeve 48 has an internally threaded bore 62 extending therethrough. As will be described below in greater detail, a threaded portion 64 of the stem shaft 30 is meshed with the threaded bore 62 of the magnetic drive actuator 44.

As shown in FIGS. 1 and 4, the magnetic drive actuator 44 is positioned in a bore section 66 of the elongated bore 32 of the outer shell 28. The distal end of the magnetic drive actuator 44 is maintained in the bore section 66 by a shoulder 68 defined in the outer shell 28. The proximal end of the magnetic drive actuator 44 is maintained in the bore section by a pair of retaining clips 70. As such, the magnetic drive actuator 44 is free to rotate within the bore 32, but is prevented from moving axially within the bore 32.

As shown in FIG. 1, the threaded portion 64 of the stem shaft 30 is threaded through the threaded bore 62 of the magnetic drive actuator 44. As such, rotation of the magnet 46 (and hence the sleeve 48) causes axial movement of the stem shaft 30. Specifically, rotation of the sleeve 48 causes the threads of the sleeve 48 to engage the threads of the shaft 30 which in turn axially moves the shaft 30 into or out of the bore 32 (depending on the direction of rotation of the sleeve 48). For example, rotation of the magnet 46 (and hence the sleeve 48) in the general direction of arrow 122 of FIG. 6 causes extension of the stem shaft 30 as indicated by arrow 124. Conversely, rotation of the magnet 46 (and hence the sleeve 48) in the general direction of arrow 126 of FIG. 6 causes retraction of the stem shaft 30 as indicated by arrow 128.

The stroke of the stem shaft 30 is limited distally by the depth of the elongated bore 32. A screw 72 is threaded through a hole 74 in the sidewall of the outer shell 28. The tip of the screw 72 translates within a slot 76 defined in the side of a shaft portion 78 of the stem shaft 30. Such a configuration prevents rotation of the stem shaft 30 relative to the outer shell 28. Moreover, the screw 72 engages the distal side wall of the slot 76 to limit the stroke of the stem shaft 30.

Figure 5:
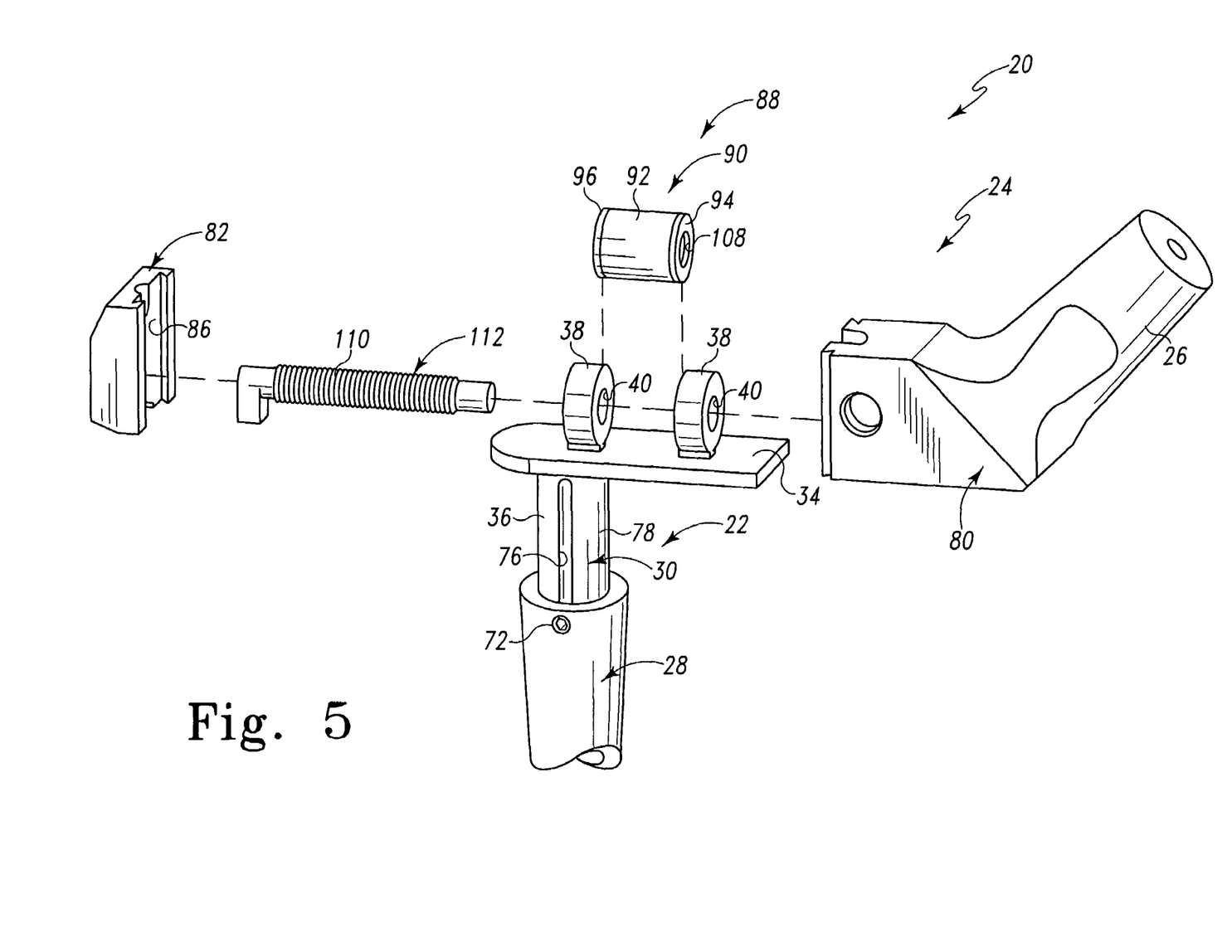
FIG. 5 is an exploded perspective view of the head of the femoral prosthesis of FIG. 1.

As shown in FIGS. 1 and 5, the head 24 includes a pair of head components. In the exemplary embodiment described herein, the head 24 includes medial head component 80 and a lateral head component 82. The neck 26 of the head 24 is defined in the medial head component 80. As shown in FIGS. 1 and 5, the medial head component 80 and the lateral head component 82 are secured to one another by the use of a dovetail joint. As such, the head components move in unison in the medial/lateral direction along the platform 34 of the stem shaft 30.

The medial head component 80 has a cavity 84 defined therein. The cavity 84 of the medial head component 80 houses an actuator 88 which is operable to bi-directionally move the head components 80, 82 relative to the platform 34 of the stem shaft 30. The actuator 88 may be embodied as any type of actuator for post-operatively moving the medial head component 80 and the lateral head component 82 relative to the stem 22. In particular, the actuator 88 is operable to extend the head 24 thereby increasing the offset of the prosthesis 20, and is also operable to retract the head 24 thereby decreasing the offset of the prosthesis 20. In the exemplary embodiment described herein, the actuator 88 is embodied as a magnetic drive actuator 90 that is operated by an external (e.g., trans-cutaneous) electromagnetic source.

As shown in FIG. 3, the magnetic drive actuator 90 includes a magnet 92, a sleeve 94, and a cap 96. The magnet 92 may be constructed with any type of implantable magnetic material, whereas the sleeve 94 and the cap 96 may be made from implantable non-magnetic materials such as cobalt chrome or titanium. In the exemplary embodiment described herein, the magnet 92 is embodied as a cylindrically-shaped body 98 having a bore 100 extending therethrough. The bore 100 has an internal hex-shaped configuration which corresponds with an external hex-shaped body 102 of the sleeve 94. An annular flange 104 is secured to one end of the hex-shaped body 102 of the sleeve 94. An annular rim 106 is secured to the other end of the hex-shaped body 102 of the sleeve 94. As shown in FIG. 3, the cap 96 is press fit or otherwise secured onto the rim 106. As such, the magnet 92 is retained on the sleeve 94 on one end by the flange 104 and on the other end by the cap 96. The interface of the hex-shaped surfaces facilitates transfer of rotational force from the magnet 92 to the sleeve 94. The sleeve 94 has an internally threaded bore 108 extending therethrough. As will be described below in greater detail, a threaded portion 110 of a head shaft 112 is meshed with the threaded bore 108 of the magnetic drive actuator 90.

As shown in FIG. 1, the magnetic drive actuator 90 is positioned in the actuator cavity 84 of the head components 80. The magnetic drive actuator 90 is positioned between the flanges 38 extending out of the platform 34 of the stem shaft 30. As such, the magnetic drive actuator 90 is free to rotate, but is prevented from moving axially by the flanges 38.

As shown in FIG. 1, the head shaft 112 extends between the head medial head component 80 and the lateral head component 82. The medial end of the head shaft 112 is positioned in a blind bore 114 defined in the medial head component 80. The lateral end of the head shaft 112 has a generally rectangularly shaped flange 116 extending therefrom. The flange 116 is positioned in a corresponding cavity 86 defined in the lateral head component 82 thereby preventing rotation of the head shaft 112. The threaded portion 110 of the head shaft 112 is threaded through the threaded bore 108 of the magnetic drive actuator 90. As such, rotation of the magnet 92 (and hence the sleeve 94) causes axial movement of the head components 80, 82 relative to the stem shaft 30. Specifically, rotation of the sleeve 94 causes the threads of the sleeve 94 to engage the threads of the head shaft 112 which in turn causes axial movement of the head shaft 112 thereby moving the head components 80, 82 along the platform 34 of the stem shaft 30. For example, rotation of the magnet 92 (and hence the sleeve 94) in the general direction of arrow 130 of FIG. 7 causes movement of the head components 80, 82 in the medial direction (as indicated by arrow 132) thereby increasing the offset of the prosthesis 20. Conversely, rotation of the magnet 92 (and hence the sleeve 94) in the general direction of arrow 134 of FIG. 7 causes movement of the head components 80, 82 in the lateral direction (as indicated by arrow 136) thereby decreasing the offset of the prosthesis 20.

Implantation of the femoral prosthesis 20 will now be described in greater detail. Prior to implantation of the stem 22, the patient's femur is surgically prepared. Specifically, the patient's femur is, for example, reamed and/or broached to form the bore in the medullary canal. Thereafter, the bore is filled, or partially filled, with bone cement. The bone cement may then be allowed to "set-up" for a period of time. Thereafter, the stem 22 is implanted into the femur. Specifically, the distal tip of the stem 22 is first advanced into the opening in the proximal end portion of the prepared femur and thereafter advanced down the medullary canal. The head 24 of the prosthesis 20 extends out of the medullary canal of the femur.

In such a way, the femoral prosthesis 20 may be utilized to secure the patient's femur for movement relative to the patient's pelvis. In particular, when implanted in such a manner, the spherically-shaped prosthetic femoral head (not shown) secured to the neck 26 of the head 24 is positioned to bear on either the patient's natural acetabulum or a prosthetic socket in the form of a prosthetic acetabular cup (not shown) which has been implanted into the patient's pelvis to replace his or her acetabulum. As a result, the femoral prosthesis 20 and the natural or artificial acetabulum collectively function as a system which replaces the natural "ball and socket" joint of the patient's hip.

Subsequent to implantation of the femoral prosthesis 20, it may become desirable to adjust the prosthesis 20. The prosthesis 20 may be adjusted along a number of different axes. For example, the prosthesis 20 may be adjust along a first axis to change the length of the prosthesis, and adjusted along a second axis to change the offset of the prosthesis.

To increase the length of the prosthesis 20, such as may be needed from time to time when the prosthesis 20 is implanted in a growing child, an external signal generating device 118 may be used. The signal generating device 118 is operated to generate a magnetic field, such as a parallel magnetic field, which drives (i.e., rotates) the magnetic drive actuator 44 in the general direction of arrow 122 of FIG. 6. As described above, such rotation of the magnet 46 (and hence the sleeve 48) of the magnetic drive actuator 44 causes axial movement of the stem shaft 30. Specifically, rotation of the sleeve 48 in the general direction of arrow 122 causes the threads of the sleeve 48 to engage the threads of the shaft 30 which in turn extends the shaft 30 out of the bore 32 (as indicated by arrow 124 in FIG. 6). Such extension of the stem shaft 30 increases the length of the prosthesis 20. It should be appreciated that the signal generating device 118 may be operated to increase the length of the prosthesis by a desired amount. It should also be appreciated that the signal generating device 118 effectuates rotation of the magnetic drive actuator 44 trans-cutaneously thereby eliminating the need to surgically gain access to the prosthesis 20 to increase the length thereof.

Figure 6:
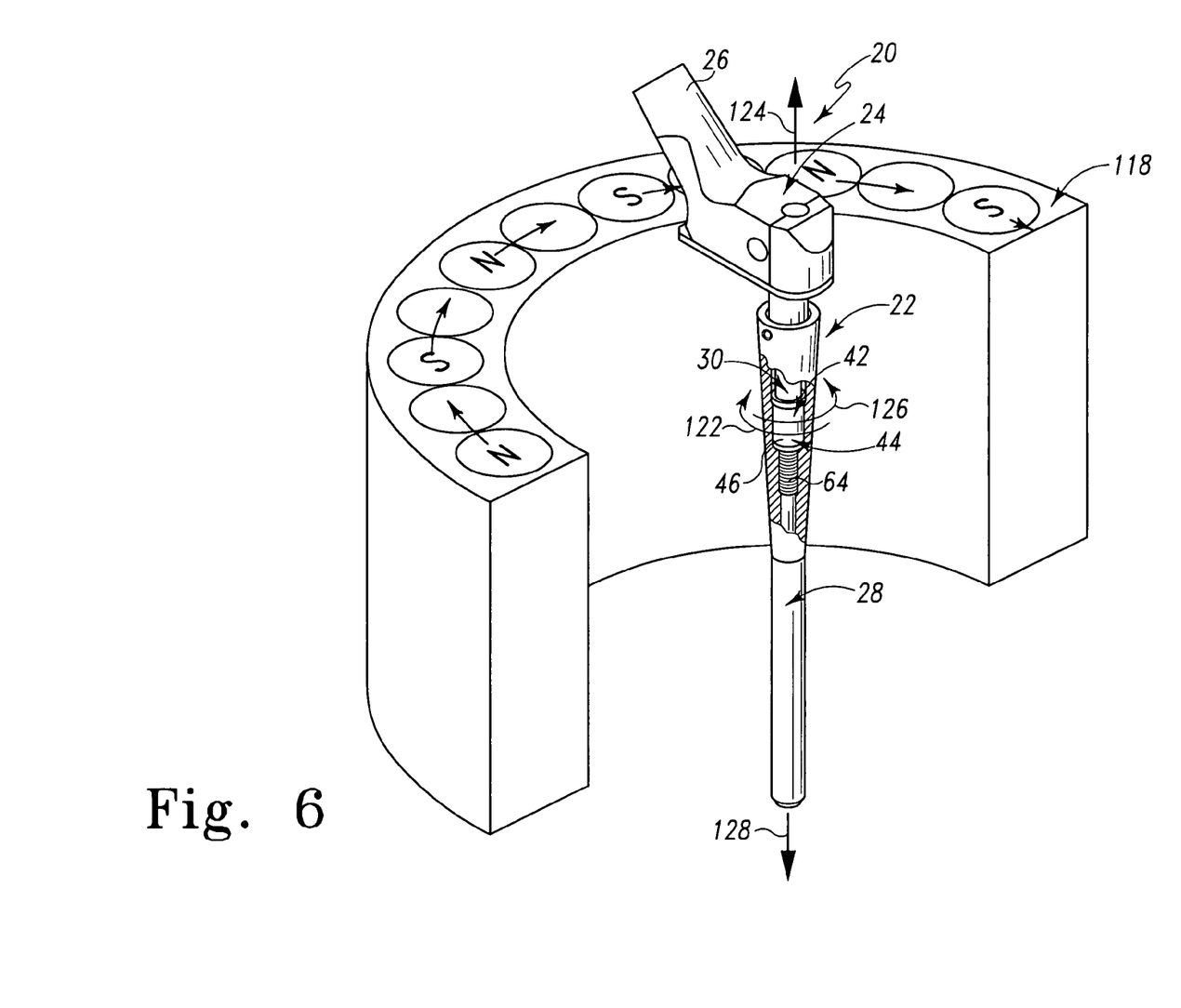
FIG. 6 is a perspective view showing the length of the femoral prosthesis of FIG. 1 being adjusted by an external signal generator.

Conversely, to decrease the length of the prosthesis 20, such as may be needed for contraction of the femur, the external signal generating device 118 may be operated to generate a magnetic field, such as a parallel magnetic field, which drives (i.e., rotates) the magnetic drive actuator 44 in the general direction of arrow 126 of FIG. 6. As described above, such rotation of the magnet 46 (and hence the sleeve 48) of the magnetic drive actuator 44 causes axial movement of the stem shaft 30. Specifically, rotation of the sleeve 48 in the general direction of arrow 126 causes the threads of the sleeve 48 to engage the threads of the shaft 30 which in turn retracts the shaft 30 into the bore 32 (as indicated by arrow 128 in FIG. 6). Such retraction of the stem shaft 30 decreases the length of the prosthesis 20. It should be appreciated that the signal generating device 118 may be operated to decrease the length of the prosthesis by a desired amount. It should also be appreciated that the signal generating device 118 effectuates rotation of the magnetic drive actuator 44 trans-cutaneously thereby eliminating the need to surgically gain access to the prosthesis 20 to decrease the length thereof.

To increase the offset of the prosthesis 20, such as may be needed from time to time subsequent to when the prosthesis 20 is implanted, an external signal generating device 120 (or the signal generating device 118 if it so configured) may be used. The signal generating device 120 is operated to generate a magnetic field, such as an end-to-end magnetic field, which drives (i.e., rotates) the magnetic drive actuator 90 in the general direction of arrow 130 of FIG. 7. As described above, rotation of the magnet 92 (and hence the sleeve 94) of the magnetic drive actuator 90 causes axial movement of the head components 80, 82 relative to the stem 22. Specifically, rotation of the sleeve 94 in the general direction of arrow 130 causes the threads of the sleeve 94 to engage the threads of the head shaft 112 which in turn causes axial movement of the head shaft 112 thereby moving the head components 80, 82 in the medial direction (as indicated by arrow 132) relative to the platform 34 of the stem shaft 30 which increases the offset of the prosthesis 20. It should be appreciated that the signal generating device 120 may be operated to increase the offset of the prosthesis 20 by a desired amount. It should also be appreciated that the signal generating device 120 effectuates rotation of the magnetic drive actuator 90 trans-cutaneously thereby eliminating the need to surgically gain access to the prosthesis 20 to change the offset thereof.

Figure 7:
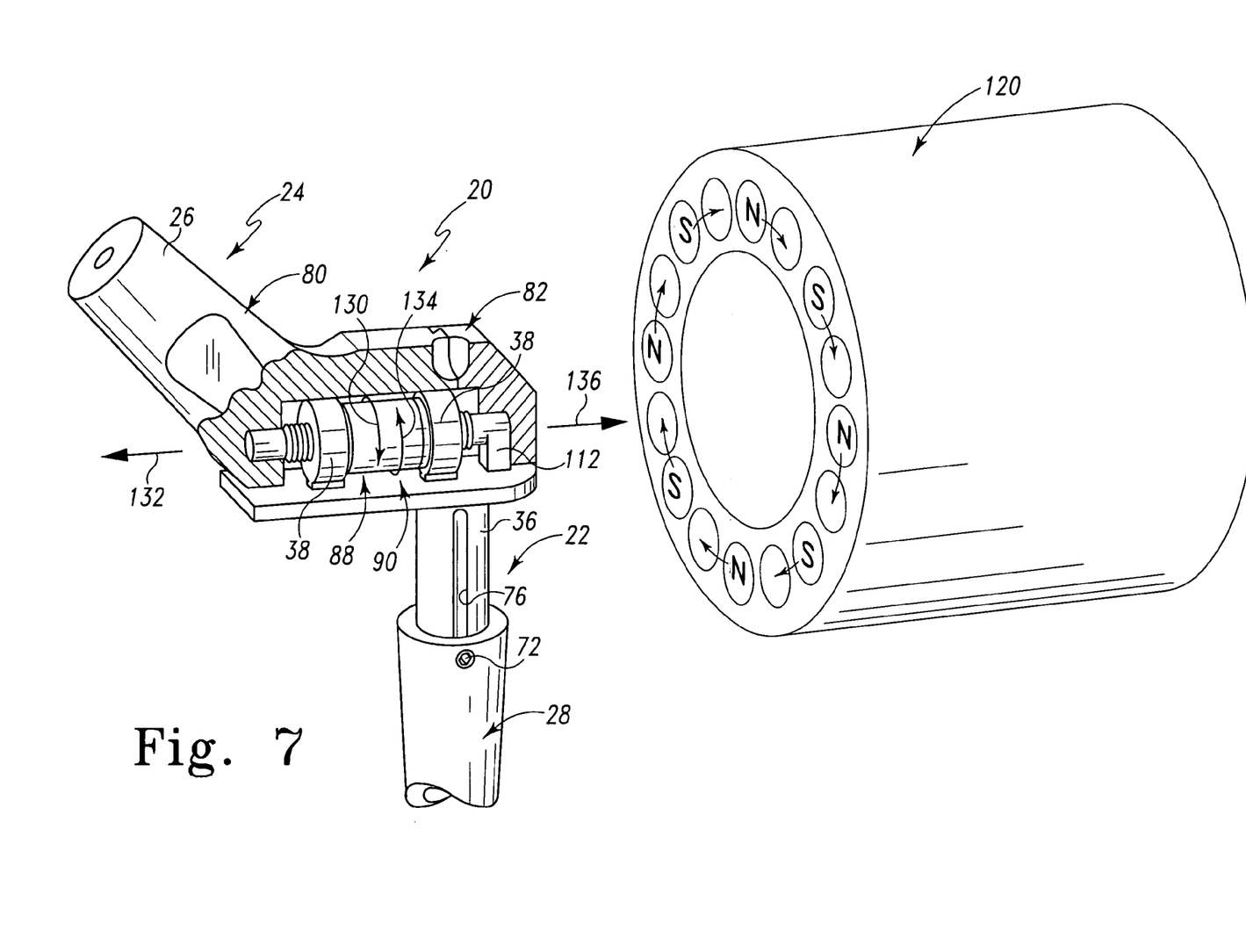
FIG. 7 is a view similar to FIG. 6, but showing the offset of the femoral prosthesis being adjusted by the external signal generator.

To decrease the offset of the prosthesis 20, such as may be needed from time to time subsequent to when the prosthesis 20 is implanted, the external signal generating device 120 may be operated to generate a magnetic field, such as an end-to-end magnetic field, which drives (i.e., rotates) the magnetic drive actuator 90 in the general direction of arrow 134 of FIG. 7. As described above, rotation of the magnet 92 (and hence the sleeve 94) of the magnetic drive actuator 90 causes axial movement of the head components 80, 82 relative to the stem 22. Specifically, rotation of the sleeve 94 in the general direction of arrow 134 causes the threads of the sleeve 94 to engage the threads of the head shaft 112 which in turn causes axial movement of the head shaft 112 thereby moving the head components 80, 82 in the lateral direction (as indicated by arrow 136) relative to the platform 34 of the stem shaft 30 which decreases the offset of the prosthesis 20. It should be appreciated that the signal generating device 120 may be operated to decrease the offset of the prosthesis 20 by a desired amount. It should also be appreciated that the signal generating device 120 effectuates rotation of the magnetic drive actuator 90 trans-cutaneously thereby eliminating the need to surgically gain access to the prosthesis 20 to change the offset thereof.

As described above, although the concepts of the present disclosure have herein been exemplarily described in regard to a prosthesis for use in the performance of a hip replacement procedure, the concepts of the present disclosure may be utilized in regard to other prostheses for use in other procedures. For example, the concepts of the present disclosure may be utilized in the construction of a hip prosthesis for implanted using minimally invasive techniques. These and other hip prostheses may be used in either primary or revision procedures. The concepts of the present disclosure may also be used in the construction of an adjustable tibial tray for use in a knee procedure. The concepts of the present disclosure may also be used in the construction of a spinal implant used to treat, amongst other things, scoliosis. The concepts of the present disclosure may also be used in the construction of fracture management devices thereby providing the device with the ability to compress a fracture site through external fixators, nails, and/or plates. The concepts of the present disclosure may also be used in the construction of expandable and contractible nails for use in, amongst other things, trauma procedures.

Moreover, it should be appreciated that the prosthesis 20 may also be configured to adjust along additional axes of movement. For example, the prosthesis 20 may be embodied with an adjustable neck 26 which may be extended and retracted by use of an actuator similar to the actuators 42, 88.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. An implantable orthopaedic prosthesis, comprising:
an outer shell having an elongated bore defined therein,
a stem shaft having a first end positioned in the elongated bore and a second end extending out of the elongated bore,
a first actuator operable to move the stem shaft relative to the outer shell along a first axis,
a neck adapted to receive a prosthetic head, and
a second actuator operable to move the neck relative to the outer shell along a second axis, the second axis being different than the first axis,
wherein (i) the first actuator comprises a first magnet positioned in the elongated bore and (ii) rotation of the first magnet causes movement of the stem shaft relative to the outer shell.

2. The prosthesis of claim 1, wherein:
rotation of the first magnet in a first rotational direction causes movement of the stem shaft relative to the outer shell in a first axial direction, and
rotation of the first magnet in a second rotational direction causes movement of the stem shaft relative to the outer shell in a second axial direction, the second axial direction being different than the first axial direction.

3. The prosthesis of claim 1, wherein:
the first actuator further comprises a sleeve secured to the first magnet,
the sleeve has a threaded bore extending therethrough,
the stem shaft has a threaded shaft portion intermeshed with the threaded bore of the sleeve, and
rotation of the sleeve causes movement of the stem shaft relative to the outer shell.

4. The prosthesis of claim 3, wherein:
rotation of the sleeve in a first rotational direction causes movement of the stem shaft relative to the outer shell in a first axial direction, and rotation of the sleeve in a second rotational direction causes movement of the stem shaft relative to the outer shell in a second axial direction, the second axial direction being different than the first axial direction.

5. The prosthesis of claim 1, further comprising a first head component and a second head component, wherein:
the neck is defined in the first head component, and
the first head component and the second head component are movable relative to the outer shell along the second axis.

6. The prosthesis of claim 5, further comprising a head shaft extending between the first head component and the second head component.

7. The prosthesis of claim 6, wherein:
the second actuator comprises a second magnet, and
rotation of the second magnet causes axial movement of the head shaft thereby moving the first head component and the second head component relative to the outer shell.

8. The prosthesis of claim 7, wherein:
rotation of the second magnet in a first rotational direction causes movement of the first head component and the second head component relative to the outer shell in a first axial direction, and
rotation of the second magnet in a second rotational direction causes movement of the first head component and the second head component relative to the outer shell in a second axial direction, the second axial direction being different than the first axial direction.

9. The prosthesis of claim 7, wherein:
the second actuator further comprises a sleeve secured to the second magnet,
the sleeve has a threaded bore extending therethrough,
the head shaft has a threaded shaft portion intermeshed with the threaded bore of the sleeve, and
rotation of the sleeve causes axial movement of the head shaft thereby moving the first head component and the second head component relative to the outer shell.

10. The prosthesis of claim 9, wherein:
rotation of the sleeve in a first rotational direction causes movement of the first head component and the second head component relative to the outer shell in a first axial direction, and
rotation of the sleeve in a second rotational direction causes movement of the first head component and the second head component relative to the outer shell in a second axial direction, the second axial direction being different than the first axial direction.

11. The prosthesis of claim 1, wherein the first actuator is operable to move the stem shaft relative to the outer shell along the first axis in both a first axial direction and a second, opposite axial direction.

12. The prosthesis of claim 1, wherein the second actuator is operable to move the neck relative to the outer shell along the second axis in both a first axial direction and a second, opposite axial direction.

13. The prosthesis of claim 1, wherein:
the first actuator is operable to move the stem shaft relative to the outer shell along the first axis in both a first axial direction and a second, opposite axial direction, and
the second actuator is operable to move the neck relative to the outer shell along the second axis in both a first axial direction and a second, opposite axial direction.

14. An implantable orthopaedic prosthesis, comprising:
a stem having a first stem component and a second stem component, the first stem component and the second stem component being movable relative to one another along a first axis,
a first actuator operable to move the first stem component and the second stem component relative to one another,
a first head component movable relative to the first stem component along a second axis which is different than the first axis, and
a second actuator operable to move the first head component relative to the first stem component,
wherein (i) the first actuator comprises a first magnet and a sleeve secured to the first magnet, the sleeve having a threaded bore extending therethrough and (ii) the first stem component has a threaded shaft portion intermeshed with the threaded bore of the sleeve, and
wherein (i) rotation of the first magnet causes movement of the first stem component relative to the second stem component and (ii) rotation of the sleeve causes movement of the first stem component relative to the second stem component.

15. The prosthesis of claim 14, wherein the first actuator is operable to move the first stem component relative to the second stem component along the first axis in both a first axial direction and a second, opposite axial direction.

16. The prosthesis of claim 14, wherein the second actuator is operable to move the first head component relative to the first stem component along the second axis in both a first axial direction and a second, opposite axial direction.

17. The prosthesis of claim 14, wherein:
the first actuator is operable to move the first stem component relative to the second stem component along the first axis in both a first axial direction and a second, opposite axial direction, and
the second actuator is operable to move the first head component relative to the first stem component along the second axis in both a first axial direction and a second, opposite axial direction.

18. The prosthesis of claim 14, wherein:
rotation of the first magnet in a first rotational direction causes movement of the first stem component relative to the second stem component in a first axial direction, and
rotation of the first magnet in a second rotational direction causes movement of the first stem component relative to the second stem component in a second axial direction, the second axial direction being different than the first axial direction.

19. The prosthesis of claim 14, wherein:
rotation of the sleeve in a first rotational direction causes movement of the first stem component relative to the second stem component in a first axial direction, and
rotation of the sleeve in a second rotational direction causes movement of the first stem component relative to the second stem component in a second axial direction, the second axial direction being different than the first axial direction.

20. The prosthesis of claim 14, further comprising a head shaft contacting the first head component.

21. The prosthesis of claim 20, wherein:
the second actuator comprises a second magnet, and
rotation of the second magnet causes axial movement of the head shaft thereby moving the first head component relative to the first stem component.

22. The prosthesis of claim 21, wherein:

rotation of the second magnet in a first rotational direction causes movement of the first head component relative to the first stem component in a first axial direction, and rotation of the second magnet in a second rotational direction causes movement of the first head component relative to the first stem component in a second axial direction, the second axial direction being different than the first axial direction.

23. The prosthesis of claim 21, wherein:

the second actuator further comprises a sleeve secured to the second magnet, the sleeve has a threaded bore extending therethrough, the head shaft has a threaded shaft portion intermeshed with the threaded bore of the sleeve, and rotation of the sleeve causes axial movement of the head shaft thereby moving the first head component relative to the first stem component.

24. The prosthesis of claim 23, wherein:

rotation of the sleeve in a first rotational direction causes movement of the first head component relative to the first stem component in a first axial direction, and rotation of the sleeve in a second rotational direction causes movement of the first head component relative to the first stem component in a second axial direction, the second axial direction being different than the first axial direction.

25. An implantable orthopaedic prosthesis, comprising:

an outer shell having an elongated bore defined therein, a stem shaft having a first end positioned in the elongated bore and a second end extending out of the elongated bore, a first magnet positioned in the elongated bore, the first magnet being rotatable relative to the stem shaft, and a sleeve secured to the first magnet, wherein the sleeve has a threaded bore extending therethrough, the stem shaft has a threaded shaft portion intermeshed with the threaded bore of the sleeve, rotation of the sleeve causes movement of the stem shaft relative to the outer shell, and rotation of the first magnet causes movement of the stem shaft relative to the outer shell.

26. The prosthesis of claim 25, wherein:

rotation of the first magnet in a first rotational direction relative to the stem shaft causes movement of the stem shaft relative to the outer shell in a first axial direction, and rotation of the first magnet in a second rotational direction relative to the stem shaft causes movement of the stem shaft relative to the outer shell in a second axial direction, the second axial direction being different than the first axial direction.

27. The prosthesis of claim 25, wherein:

rotation of the sleeve in a first rotational direction relative to the stem shaft causes movement of the stem shaft relative to the outer shell in a first axial direction, and rotation of the sleeve in a second rotational direction relative to the stem shaft causes movement of the stem shaft relative to the outer shell in a second axial direction, the second axial direction being different than the first axial direction.

28. An implantable orthopaedic prosthesis, comprising:

an outer shell having an elongated bore defined therein, a stem shaft having a first end positioned in the elongated bore and a second end extending out of the elongated bore, a first magnet positioned in the elongated bore, the first magnet being rotatable relative to the stem shaft, a first head component having a neck adapted to receive a prosthetic head, and a second magnet, the second magnet being rotatable relative to the first head component, wherein rotation of the first magnet causes movement of the stem shaft relative to the outer shell and rotation of the second magnet causes movement of the first head component relative to the outer shell.

29. The prosthesis of claim 28, wherein:

rotation of the second magnet in a first rotational direction causes movement of the first head component relative to the outer shell in a first axial direction, and rotation of the second magnet in a second rotational direction causes movement of the first head component relative to the outer shell in a second axial direction, the second axial direction being different than the first axial direction.

30. The prosthesis of claim 29, further comprising a second head component, wherein:

the first head component is secured to the second head component, the first head component defines an actuator cavity, and the second magnet is positioned in the actuator cavity.

31. The prosthesis of claim 30, further comprising a head shaft extending between the first head component and the second head component, wherein rotation of the second magnet causes axial movement of the head shaft thereby moving the first head component and the second head component relative to the outer shell.

32. The prosthesis of claim 31, further comprising a sleeve secured to the second magnet, wherein:

the sleeve has a threaded bore extending therethrough, the head shaft has a threaded shaft portion intermeshed with the threaded bore of the sleeve, and rotation of the sleeve causes axial movement of the head shaft thereby moving the first head component and the second head component relative to the outer shell.

33. The prosthesis of claim 32, wherein:

rotation of the sleeve in a first rotational direction causes movement of the first head component and the second head component relative to the outer shell in a first axial direction, and rotation of the sleeve in a second rotational direction causes movement of the first head component and the second head component relative to the outer shell in a second axial direction, the second axial direction being different than the first axial direction.

* * * * *